United States Patent
Giuliano et al.

(10) Patent No.: US 9,969,989 B2
(45) Date of Patent: May 15, 2018

(54) CAROTENOID DIOXYGENASE AND METHODS FOR THE BIOTECHNOLOGICAL PRODUCTION IN MICROORGANISMS AND PLANTS OF COMPOUNDS DERIVED FROM SAFFRON

(71) Applicant: AGENZIA NAZIONALE PER LE NUOVE TECNOLOGIE, L'ENERGIA E LO SVILUPPO ECONOMICO SOSTENIBILE (ENEA), Rome (IT)

(72) Inventors: Giovanni Giuliano, Rome (IT); Paola Ferrante, Rome (IT); Sarah Frusciante, Avellino (IT); Gianfranco Diretto, Rome (IT); Marco Pietrella, Montefano (IT); Salim Al-Babili, Thuwal (SA)

(73) Assignee: AGENZIA NAZIONALE PER LE NUOVE TECNOLOGIE, L'ENERGIA E LO SVILUPPO ECONOMICO SOSTENIBILE (ENEA), Rome RM (IT)

( * ) Notice: Subject to any disclaimer, the term of this patent is extended or adjusted under 35 U.S.C. 154(b) by 0 days. days.

(21) Appl. No.: 15/327,575

(22) PCT Filed: Jul. 23, 2015

(86) PCT No.: PCT/IB2015/055577
§ 371 (c)(1),
(2) Date: Jan. 19, 2017

(87) PCT Pub. No.: WO2016/012968
PCT Pub. Date: Jan. 28, 2016

(65) Prior Publication Data
US 2017/0175089 A1    Jun. 22, 2017

(30) Foreign Application Priority Data
Jul. 23, 2014  (IT) .............................. RM2014A0415

(51) Int. Cl.
| | | |
|---|---|---|
| C07C 1/00 | (2006.01) | |
| C12N 9/02 | (2006.01) | |
| C12N 15/82 | (2006.01) | |
| C12P 7/24 | (2006.01) | |
| C12P 7/44 | (2006.01) | |

(52) U.S. Cl.
CPC ......... *C12N 9/0083* (2013.01); *C12N 15/825* (2013.01); *C12N 15/8243* (2013.01); *C12P 7/24* (2013.01); *C12P 7/44* (2013.01)

(58) Field of Classification Search
CPC .............................. C12N 9/0069; C07C 1/00
See application file for complete search history.

(56) References Cited

FOREIGN PATENT DOCUMENTS

| WO | WO 2013/021261 | 3/2013 |
|---|---|---|
| WO | WO 2015/132411 | 9/2015 |

OTHER PUBLICATIONS

Alagna et al., "Comparative 454 pyrosequencing of transcripts from two olive genotypes during fruit development.", BMC Genomics, 10(1):399 (Aug. 2009).
Alder et al., "Carotenoid oxygenases involved in plant branching catalyse a highly specific conserved apocarotenoid cleavage reaction.", Biochem J, 416(2):289-296 (2008).
Bouvier et al., "Oxidative remodeling of chromoplast carotenoids: Identification of the carotenoid dioxygenase CsCCD and CsZCD genes involved in Crocus secondary metabolite biogenesis.", Plant Cell, 15(1):47-62 (Jan. 2003).
Caballero-Ortega et al., "HPLC quantification of major active components from 11 different saffron (Crocus sativus L.) sources.", Food Chemistry, 100(3):1126-1131 (Dec. 2007).
Fantini et al., "Dissection of Tomato Lycopene Biosynthesis through Virus-Induced Gene Silencing.", Plant Physiol, 163(2):986-998 (Oct. 2013).
Fernandez et al., "Biology, biotechnology and biomedicine of saffron.", Recent research developments in plant science, 2:127-159 (2004).
Frusciante et al., "Novel carotenoid cleavage dioxygenase catalyzes the first dedicated step in saffron crocin biosynthesis.", PNAS, 111(33):12246-12251 (Aug. 2014).
Gomez-Gomez et al., "Understanding Carotenoid Metabolism in Saffron Stigmas: Unraveling aroma and colour formation.", Functional Plant Science and Biotechnology, 2:56-63 (Apr. 2010).
Jefferson et al., "Assaying chimeric genes in plants: the GUS gene fusion system.", Plant Mol Biol Reporter, 5 (4):387-405 (1987).
Kallberg et al., "Template-based protein structure modeling using the RaptorX web server.", Nat Protoc, 7 (8):1511-1522 (Jul. 2012).
Moraga et al., "Glucosylation of the saffron apocarotenoid crocetin by a glucosyltransferase isolated from Crocus sativus stigmas.", Planta, 219(6):955-966 (Nov. 2004).
Moraga et al., "Metabolite and target transcript analyses during Crocus sativus stigma development.", Phytochemistry, 70(8):1009-1016 (Jun. 2009).
Nagatoshi et al., "UGT75L6 and UGT94E5 mediate sequential glucosylation of crocetin to crocin in Gardenia asminoides", FEB Letters, 586(7):1055-1061 (Mar. 2012).
Prada-Cabrero et al., "Retinal Biosynthesis in fungi: characterization of the carotenoid oxygenase CarX from Fusarium fujikuroi.", Eukaryot Cell, 6(4):650-657 (Apr. 2007).
Qi et al., "Crocin precents retinal ischaemia/reperfusion injury-induced apoptosis in retinal ganglion cells through the Pi3K/Akt signalling pathway.", Exp Eye Res, 107:44-51 (Feb. 2013).
Reyes et al., "Agrobacterium tumefaciens-mediated transformation of maize endosperm as a tool to study endosperm cell biology." Plant Physiol, 153(2):624-631 (Jun. 2010).

(Continued)

*Primary Examiner* — Maryam Monshipouri
(74) *Attorney, Agent, or Firm* — McDonnell Boehnen Hulbert & Berghoff LLP (57) ABSTRACT

The present invention relates to a new carotenoid dioxygenase and methods for the biological production in microorganisms and plants of compounds with high added value derived from saffron.

13 Claims, 4 Drawing Sheets

(56) References Cited

OTHER PUBLICATIONS

Rubio et al., "Cytosolic and plastoglobule-targeted carotenoid dioxygenases from Crocus sativus are both involved in beta-ionone release.", JBC, 283(36):24816-24825 (May 2008).

Saitou et al., "The neighbor-joining method: a new method for reconstructing phylogenetic trees.", Mol Biol Evol, 4(4):406-425 (1987).

Sui et al., "Structural basis of carotenoid cleavage: from bacteria to mammals.", Arch Biochem Biophys, 539(2):203-213 (Nov. 2013).

Trautmann et al., "The ORF slr0091 of *Synechocystis* sp. PCC6803 encodes a high-light induced aldehyde dehydrogenase converting apocarotenals and alkanals." FEBS J, 280(15):3685-3696 (May 2013).

Yamauchi et al., "Crocetin prevents retinal degeneration induced by oxidative and endoplasmic reticulum stresses via inhibition of caspase activity.", European J of Pharmacology, 650(1):110-119 (Oct. 2010).

EBI Accession No. ACD62475, "Crocus sativus carotenoid cleavage dioxygenase 2" p. 1-2.

EBI Accession No. KJ541749, "Crocus sativus crotenoid cleavage dioxygenase 2 (CCD2) mRNA, complete cds" p. 1-2.

International Search Report and Written Opinion for International Application No. PCT/IB2015/055577, dated Dec. 21, 2015, pp. 1-13.

CAROTENOID DIOXYGENASE AND METHODS FOR THE BIOTECHNOLOGICAL PRODUCTION IN MICROORGANISMS AND PLANTS OF COMPOUNDS DERIVED FROM SAFFRON

This application is a national stage application under 35 U.S.C. § 371 of International Application No. PCT/IB2015/055577, filed Jul. 23, 2015, which claims the benefit of RM2014A000415, filed Jul. 23, 2014, the disclosures of each of which are explicitly incorporated herein by reference.

The present invention relates to a new carotenoid dioxygenase and methods for the biological production in microorganisms and plants of compounds with high added value derived from saffron.

The present invention relates in particular to genes, proteins and methods for the production of apocarotenoids of saffron in vitro systems, in engineered strains of *E. coli* and in plant tissues. More specifically, the present invention relates to the isolation and characterisation of the saffron gene CCD2, which codes for an enzyme with dioxygenase activity that cleaves carotenoids (Carotenoid Cleavage Dioxygenase: CCD). The overexpression of this gene in an engineered microorganism that accumulates zeaxanthin, such as *E. coli* or in a plant tissue rich in zeaxanthin, such as corn endosperm, determines the production of crocetin dialdehyde and of crocetin, respectively. The invention also relates to the development of an in vitro assay to study the activity of said dioxygenase.

Figure 1:
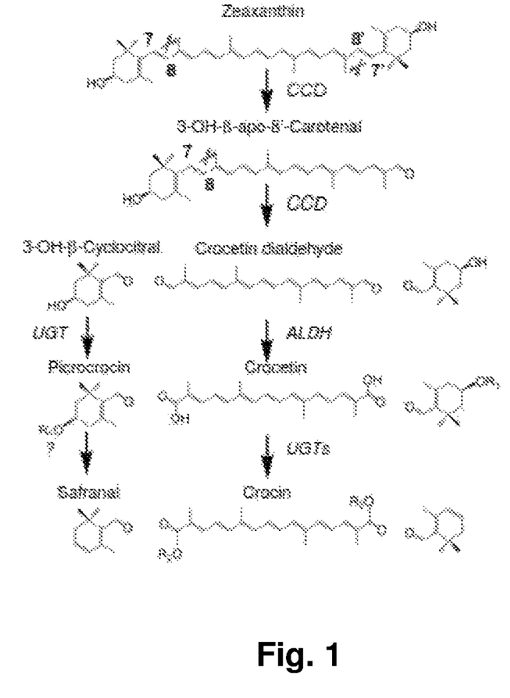

*Crocus sativus* L. (Iridaceae) is a perennial, triploid, sterile plant propagated vegetatively and cultivated in mild areas from Spain to Kashmir (1). Its dried stigmas constitute the spice saffron, which is commonly considered to be the most costly in the world with prices ranging from 2,000 to 7.000 0 € /Kg. The high costs of saffron are caused by the necessary manual work associated with the harvesting of the stigmas: 1 Kg of dried saffron requires the manual harvesting of approximately 150,000 flowers (1). The stigmas of saffron accumulate a series of apocarotenoid compounds: crocetin and the glycosylated forms thereof (crocins), which are responsible for the red coloration of the stigmas; picrocrocin, which is responsible for the bitter taste of saffron; and safranal, which is responsible for the pungent aroma of saffron (2). In addition to being high-value ingredients added to food, the apocarotenoid compounds of saffron have cosmetic and medical applications (1), including, by way of non-limiting example, the protective function against degenerative diseases of the retina demonstrated for crocetin and crocins (3, 4). Under consideration of such applications and under consideration of the high cost of saffron apocarotenoids, which are currently produced by means of costly extraction processes, there is an industrial interest in the development of methods for the economical biotechnological production thereof by means of expression of the enzymes involved in the biosynthesis thereof in microbial systems or in plants with high productivity. The biosynthesis of such compounds starts with the symmetrical cleaving, in positions 7,8 and 7'8', of zeaxanthin by means of a dioxygenase (CCD, Carotenoid Cleavage Dioxygenase) (FIG. 1). The two products of the cleavage of zeaxanthin, i.e. 3-OH-β-cyclocitral and crocetin dialdehyde, are dehydrogenated and glycosylated in order to produce, respectively, picrocrocin and crocins. The glucosyltransferases responsible for the glycosylation reaction have been described in saffron and *Gardenia* (5) (6). With regard to the first biosynthetic step, some authors have reported that an enzyme called ZCD cleaves zeaxanthin symmetrically at positions 7,8/7',8', producing crocetin dialdehyde (7), which is an observation contradicted by subsequent works (8). The modelling of the three-dimensional structure of ZCD has shown that ZCD is an incomplete enzyme, devoid of blade VII of the conserved β-propeller structure (9), consistent with the absence of enzymatic activity of ZCD (8). Consequently, it is not currently possible by biotechnological methods to produce the apocarotenoid compounds of saffron, and in particular crocetin and crocins, since the identification of the first enzyme of the biosynthetic pathway, i.e. CCD, which is responsible for the symmetrical cleaving in positions 7,8 and 7',8' of zeaxanthin, is still uncertain.

The object of the present invention is to provide a new carotenoid dioxygenase and methods for the biological production in microorganisms and plants of compounds of high added value derived from saffron.

The above-mentioned and further objects of the invention, as will become clear from the following description, are achieved by means of a gene coding for a Carotenoid Dioxygenase enzyme, an enzyme coded in this way, and methods for producing crocin precursors as claimed in the corresponding independent claims.

The present invention will be better understood from the following detailed description of some preferred embodiments, provided with reference to the accompanying drawings, in which the corresponding figures show:

FIG. 1 Biosynthetic pathway of apocarotenoids in saffron. Proposed biosynthetic pathway for the biosynthesis of the apocarotenoids. Zeaxanthin is cleaved in positions 7,8 and 7',8' by the activity of a CCD. The cleavage product $C_{20}$, crocetin dialdehyde, is converted into crocetin from an aldehyde dehydrogenase, then into crocin by the activity of at least two UDPG glycosyltransferases. The product $C_{10}$, 3-OH-β-cyclocitral, is converted into picrocrocin from a UDPG-glycosyltransferase, and then into safranal.

FIG. 2 Expression and structural characteristics of saffron CCDs. (A) Expression of various CCDs during the development of the stigma of saffron. The graph above, the "heatmap", shows the kinetics of accumulation of the different apocarotenoids; (B) Phylogenetic relationships between the saffron CCDs (Cs), *Arabidopsis* (At), rice (Os), tomato (S1), lettuce (Ls), clementine (Cc) and *Synechocystis* (Sy), evaluated by means of the Neighbor-Joining method; (C) Three-dimensional models of the ACO (Apocarotenoid Cleavage Oxygenase) of *Synechocystis* and of the CCD2, ZCD and CCD4a of *Crocus sativus*. The ZCD is missing blade VII of the β-propeller structure (shaded).

FIG. 4 Affinity assay in vitro. (A) Cleaving of zeaxanthin in the in vitro assay from extracts of *E. coli* expressing CCD2. (B) Substrates that are not cleaved in vitro from CCD2. (C) Substrates that are cleaved in vitro from CCD2 and position of the cleaving.

The present invention will now be described in detail with reference to the figures.

Figure 2:
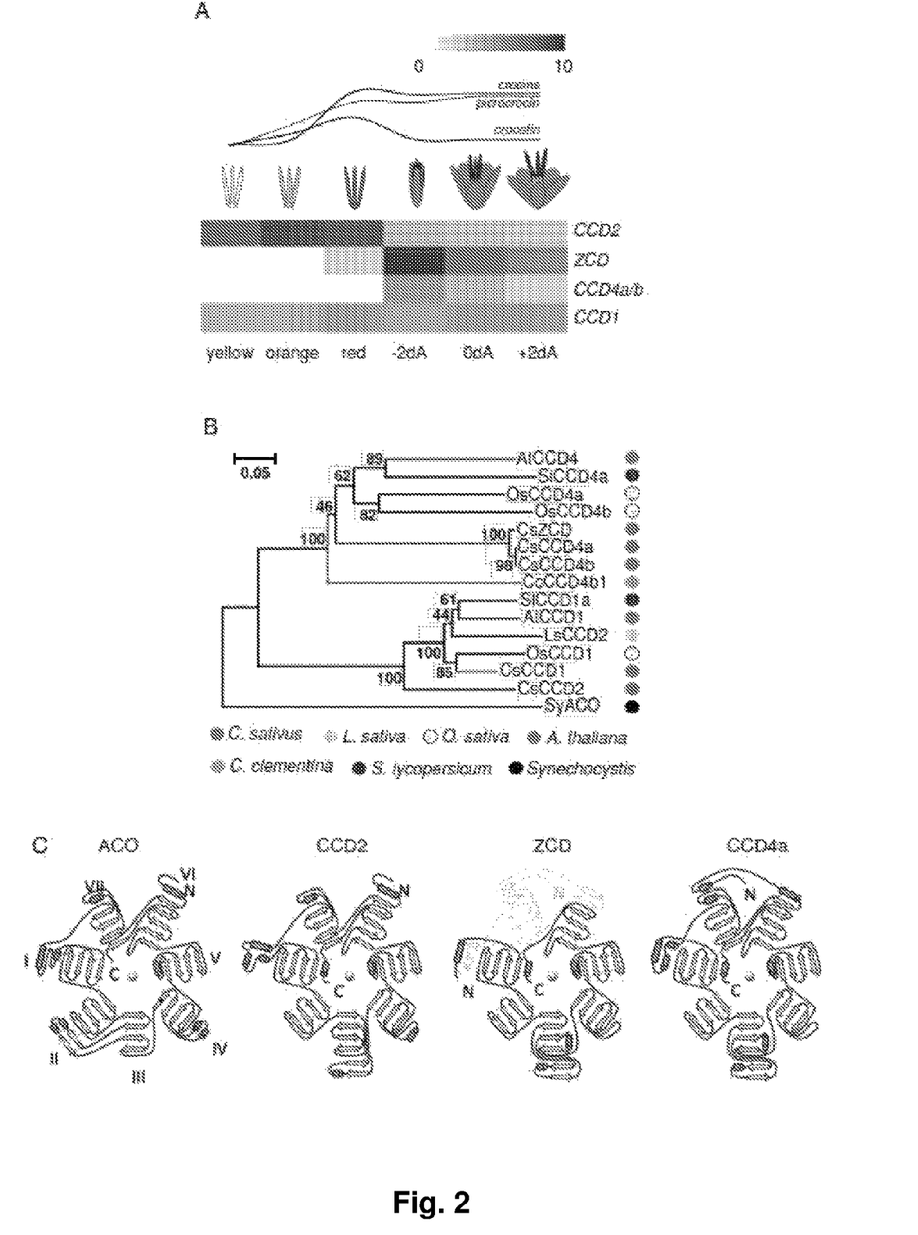
Figure 3:
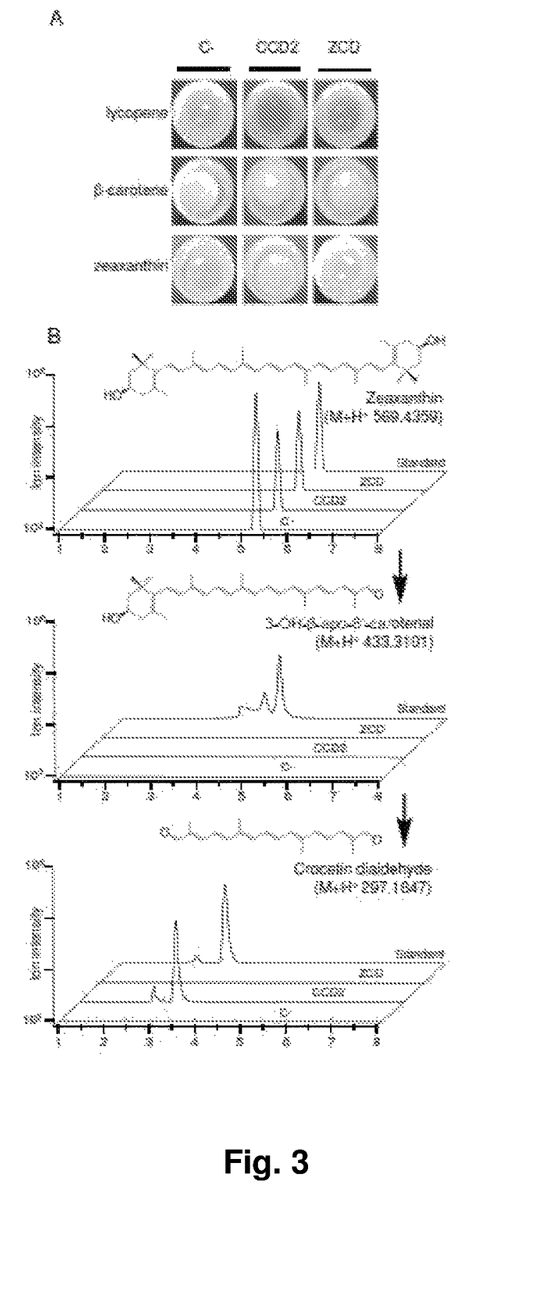
FIG. 3 CCD2 expressed in *E. coli* converts zeaxanthin with formation of crocetin dialdehyde. (A) Cells of *E. coli* that accumulate lycopene, β-carotene or zeaxanthin have been transformed with the empty vector pThio1-DAN (C—), or with the same vector in which the CCD2 or the ZCD was cloned. The discoloration of the zeaxanthin exclusively in the cells that express CCD2 should be noted. (B) HPLC-HRMS analyses of the apocarotenoids in cells that express zeaxanthin and CCD2 after incubation at 20° C. for 16 h. These produce crocetin dialdehyde, of which the chromatographic mass and mobility is identical to that of an authentic standard.

RNA isolated from stigmas of saffron was sequenced by means of RNA-Seq 454 Titanium technology as reported in the literature (10) (FIG. 2A). The evolutionary relationships between the gene families CCD1 and CCD4 of saffron, *Arabidopsis*, rice and *Synechocystis*, were studied using the Neighbor-Joining method (11) (FIG. 2B), whilst the CCD proteins were modelled using the web server RaptorX (12) (FIG. 2C). The assays in bacteria were obtained by transforming particular strains of *E. coli* engineered to accumulate lycopene, β-carotene, and zeaxanthin, with the expression vectors pThio-DAN1-CCD2, pThio-DAN1-ZCD and pThio-DAN1 (empty vector, used as control) as indicated in the literature (13) (14) (15) (FIG. 3). The transformation of corn endosperm, in *Agrobacterium tumefaciens*-mediated manner, was obtained by cloning the coding sequence of CCD2 in the vector pBI121 (16) and by using protocols already present in the literature (17). The strain of *E. coli* BL21 (p-Gro7) was used to assay the activity in vitro of CCD2: the raw protein extracts were prepared and incubated with the appropriate substrates and extracts as described before (14) (FIG. 4). All the analyses directed to the identification and quantification of the carotenoids and apocarotenoids were performed using a mass spectrometry platform LTQ-Orbitrap coupled with a high-pressure liquid chromatography (HPLC) system and with a diode array detector (DAD) (ThermoFisher Scientific); the chromatographic separation was obtained using a $C_{30}$ column with inverse phase, whereas for positive ionisation an APCI (Atmospheric Pressure Chemical Ionization) source was selected (18).

The present invention will be better illustrated with reference to the following practical examples, which are provided by way of non-limiting explanation.

Example 1. Identification of the Gene CCD2 Expressed in the Stigmas of *C. sativus*

The transcripts CCD4 and ZCD were expressed around anthesis, when the biosynthesis of crocetin, of picrocrocin and of crocins is essentially complete. Only CCD2 is expressed in the early stages of development, which actively synthesise apocarotenoids (FIG. 2A) (19). The CCD2 protein of *Crocus* is a member of a new sub-family of CCDs, similar to, but distant from, the CCD1s (FIG. 2B). CCD2 has all 7 blades forming the β-propeller structure, preserved in all CCDs, whilst ZCD is missing blade VII (FIG. 2C).

Example 2. Demonstration that the Gene CCD2, Expressed in the Bacteria *E. coli* Genetically Modified to Accumulate Zeaxanthin, Converts Zeaxanthin with Production of Crocetin Dialdehyde and that the Gene ZCD does not Possess Such Property The coding sequences of the genes CCD2 and ZCD were cloned in the vector pThio-DAN1, which allows an inducible expression in *E. coli* induced from arabinose. The recombinant proteins were expressed in three strains of *E. coli* that accumulate lycopene, β-carotene and zeaxanthin (FIG. 3A) (13) (14). Whilst no discoloration and no cleavage product were observed in the strains of *E. coli* that accumulate lycopene and β-carotene following the expression of CCD2 or of ZCD (FIG. 3A), the expression of CCD2 in the strain of *E. coli* that accumulates zeaxanthin lead to clear discoloration of the bacterial cells (FIG. 3A). The HPLC analyses coupled with high-resolution mass spectrometry (LC-HRMS) showed a peak with a m/z ratio of 297.1847, which corresponds to crocetin dialdehyde, which demonstrates the same chromatographic mobility as an authentic standard of such a substance (FIG. 3B). A peak with the chromatographic and the m/z ratio (329.1747) typical of crocetin was also discernible. The ZCD, expressed in the same system, did not produce any discoloration or any cleavage product (FIG. 3A-B).

Example 3. Demonstration that the Gene CCD2 Expressed in Corn Endosperm and/or Cells of *Arabidopsis thaliana* Converts Zeaxanthin with Production of Crocetin The sequences coding CCD2 and ZCD were cloned in the binary vector pBI121 under the control of the established promoter 35S. The vectors thus obtained were used to transform corn endosperm and cells of *Arabidopsis thaliana*, which contain zeaxanthin. The endosperm transformed with CCD2 showed discoloration, which is a sign of a cleaving activity of carotenoids, compared with that transformed with a vector containing ZCD or a component of β-glucuronidase. The LC-HRMS analysis carried out on the vegetable cells that express CCD2 did not demonstrate the presence of 3-OH-β-apo-8'-carotenal or of crocetin dialdehyde, but a new peak with a ratio m/z equal to 329.1747, corresponding to crocetin, which demonstrates chromatographic mobility identical to that of an authentic standard of this substance. Such a conversion is caused by the conversion of crocetin dialdehyde to crocetin in the corn endosperm (Table 1) and in the cells of *Arabidopsis thaliana*. No cleavage product of zeaxanthin was instead produced in the corn endosperm expressing ZCD or β-glucuronidase.

Figure 4:
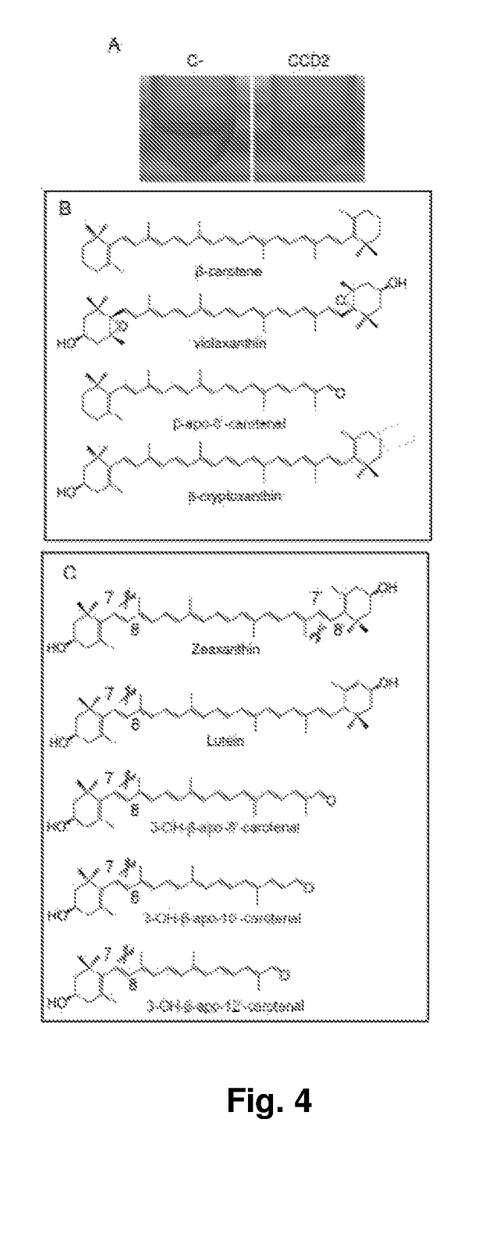

Example 4. Development and Use of an In Vitro Assay to Study the Specificity of CCD2 for the Various Carotenoids Since the strains of genetically modified *E. coli* can produce only a limited number of different carotenoids, we developed and used an in vitro assay, based on semi-purified extracts of *E. coli* that expresses CCD2, in order to study the specificity of this enzyme for the various carotenoids. In such an assay the CCD2 does not cleave β-carotene, violaxanthin, or β-apo-8'-carotenal, but cleaves the zeaxanthin producing 3-OH-β-apo-8'-carotenal, i.e. the product of the single cleave in position 7',8' (FIG. 4). ZCD, instead, does not cleave any of the carotenoids, not even zeaxanthin. 3-OH-β-apo-8'-carotenal, formed from CCD2 on the basis of the zeaxanthin in vitro, is then cleaved from the CCD2, with production of crocetin, signalling that the extracts of *E. coli* are able to convert the product of CCD2, crocetin dialdehyde, into crocetin.

TABLE 1

Relative content of carotenoids and apocarotenoids in corn endosperm transformed with plasmids expressing various enzymes

| Molecule | 35S: β-glucuronidase | 35S: CCD2 | 35S: ZCD |
|---|---|---|---|
| Lutein | 0.81 ± 0.15 | 0.48 ± 0.05** | 0.64 ± 0.09 |
| Zeaxanthin | 1.98 ± 0.33 | 0.84 ± 0.18** | 1.73 ± 0.20 |
| β-cryptoxanthin | 0.15 ± 0.03 | 0.17 ± 0.04 | 0.12 ± 0.04 |
| Crocetin | n.d. | 0.008 ± 0.002 | n.d. |

Peak areas of the ions, standardised by the internal standard, for the more abundant carotenoids and apocarotenoids. The data shown represents the mean ± SD of 4 biological repetitions.
n.d. = not detectable;
* = P value 0.05;
** = P value 0.01.

REFERENCES (1) Fernandez J A & Pandalai S G (2004) Biology, biotechnology and biomedicine of saffron. *Recent research developments in plant science*. Vol. 2:127-159.
(2) Caballero-Ortega H, Pereda-Miranda R, & Abdullaev F I (2007) HPLC quantification of major active components from 11 different saffron (*Crocus sativus* L.) sources. *Food Chemistry* 100(3):1126-1131.
(3) Yamauchi M, Tsuruma K, Imai S, Nakanishi T, Umigai N, Shimazawa M, Hara H: Crocetin prevents retinal degeneration induced by oxidative and endoplasmic reticulum stresses via inhibition of caspase activity. European journal of pharmacology 2011 650(1):110-119.
(4) Qi Y, Chen L, Zhang L, Liu W B, Chen X Y, Yang X G: Crocin prevents retinal ischaemia/reperfusion injury-induced apoptosis in retinal ganglion cells through the pi3k/akt signalling pathway. Experimental eye research 2013 107 (44-51).
(5) Moraga A R, Nohales P F, Perez J A, & Gomez-Gomez L (2004) Glucosylation of the saffron apocarotenoid crocetin by a glucosyltransferase isolated from *Crocus sativus* stigmas. *Planta* 219(6):955-966.
(6) Nagatoshi M, et al. (2012) UGT75L6 and UGT94E5 mediate sequential glucosylation of crocetin to crocin in *Gardenia jasminoides*. *FEBS Lett* 586(7):1055-1061.
(7) Bouvier F, Suire C, Mutterer J, & Camara B (2003) Oxidative remodeling of chromoplast carotenoids: Identification of the carotenoid dioxygenase CsCCD and CsZCD genes Involved in *Crocus* secondary metabolite biogenesis. *Plant Cell* 15(1):47-62.
(8) Rubio A, et al. (2008) Cytosolic and plastoglobule-targeted carotenoid dioxygenases from *Crocus sativus* are both involved in beta-ionone release. *J Biol Chem* 283 (36):24816-24825.
(9) Sui X, Kiser P D, Lintig J, & Palczewski K (2013) Structural basis of carotenoid cleavage: from bacteria to mammals. *Arch Biochem Biophys* 539(2):203-213.
(10) Alagna F, et al. (2009) Comparative 454 pyrosequencing of transcripts from two olive genotypes during fruit development. BMC Genomics 10(1):399.
(11) Saitou N & Nei M (1987) The neighbor-joining method: a new method for reconstructing phylogenetic trees. *Mol Biol Evol* 4(4):406-425.
(12) Kallberg M, et al. (2012) Template-based protein structure modeling using the RaptorX web server. *Nat Protoc* 7(8): 1511-1522.
(13) Prado-Cabrero A, Scherzinger D, Avalos J, & Al-Babili S (2007) Retinal biosynthesis in fungi: characterization of the carotenoid oxygenase CarX from *Fusarium fujikuroi*. *Eukaryot Cell* 6(4):650-657
(14) Alder A, Holdermann I, Beyer P, & Al-Babili S (2008) Carotenoid oxygenases involved in plant branching catalyse a highly specific conserved apocarotenoid cleavage reaction. *Biochem J* 416(2):289-296.
(15) Trautmann D, Beyer P, & Al-Babili S (2013) The ORF slr0091 of *Synechocystis* sp. PCC6803 encodes a high-light induced aldehyde dehydrogenase converting apocarotenals and alkanals. *FEBS J* 280(15):3685-3696.
(16) Jefferson R A (1987) Assaying chimeric genes in plants: the GUS gene fusion system. *Plant Mol Biol Reporter* 5:387-405.
(17) Reyes F C, Sun B, Guo H, Gruis D F, & Otegui M S (2010) *Agrobacterium tumefaciens*-mediated transformation of maize endosperm as a tool to study endosperm cell biology. *Plant Physiol* 153 (2): 624-631
(18) Fantini E, Falcone G, Frusciante S, Giliberto L, & Giuliano G (2013) Dissection of Tomato Lycopene Biosynthesis through Virus-Induced Gene Silencing. *Plant Physiol* 163(2):986-998.
(19) Moraga A R, Rambla J L, Ahrazem O, Granell A, & Gomez-Gomez L (2009) Metabolite and target transcript analyses during *Crocus sativus* stigma development. *Phytochemistry* 70(8): 1009-1016.

The invention claimed is:

1. A method for producing crocetin dialdehyde and/or crocetin in a recombinant host wherein the recombinant host is genetically modified to accumulate zeaxanthin, comprising transforming the recombinant host with an expression vector comprising the carotenoid cleavage dioxygenase ("CCD") enzyme encoded by the nucleotide sequence of SEQ ID NO: 1.

2. The method of claim 1, wherein said microorganisms are bacterial cells or yeast cells.

3. The method according to claim 2, wherein said bacterial cells are *E. coli* cells and said yeast cells are *S. cerevisiae* cells.

4. The method of claim 2, wherein the cells are cells that have been transformed with an expression vector p-Thio-DAN1 that comprises a nucleic acid of SEQ ID NO: 1, and wherein the expression vector is induced by arabinose and the CCD enzyme is thereby overexpressed.

5. A method for producing crocetin in vegetable cells that express zeaxanthin, comprising a step of transforming said cells with the binary vector pBI121 comprising a heterologous gene comprising the nucleotide sequence of SEQ ID NO: 1.

6. The method of claim 5, in which said cells are corn endosperm cells or *Arabidopsis thaliana* cells.

7. A recombinant host capable of producing crocetin dialdehyde and/or crocetin, comprising:

a gene encoding a heterologous carotenoid cleavage dioxygenase (CCD) enzyme having the amino acid sequence of SEQ ID NO:2, wherein the heterologous CCD enzyme is able to cleave carotenoids symmetrically in positions 7,8 and 7',8' thereby producing crocetin dialdehyde.

8. The recombinant host of claim 7, wherein the recombinant host comprises a microorganism that is a bacterial cell, or a yeast cell.

9. The recombinant host of claim 8, wherein said bacterial cells are *E. coli* cells, and said yeast cells are *S. cerevisiae* cells.

10. The recombinant host of claim 8, wherein the cells are cells that have been transformed with an expression vector p-Thio-DAN1 that comprises the nucleic acid of SEQ ID NO: 1, and wherein the expression vector is induced by arabinose and the CCD enzyme is thereby overexpressed.

11. The recombinant host of claim 7, wherein the recombinant host comprises a microorganism that is a plant cell.

12. The recombinant host of claim 11, wherein said plant cell is a vegetable cell comprising corn endosperm cells or *Arabidopsis thaliana* cells.

13. The recombinant host of claim 12, wherein the cells are cells that have been transformed with the binary vector pBI121 comprising a heterologous gene comprising the nucleotide sequence of SEQ ID NO: 1.

* * * * *

```
                         SEQUENCE LISTING

<160> NUMBER OF SEQ ID NOS: 2

<210> SEQ ID NO 1
<211> LENGTH: 1689
<212> TYPE: DNA
<213> ORGANISM: Crocus sativus

<400> SEQUENCE: 1
atggcaaata aggaggaggc agagaagagg aagaagaagc ccaaaccatt aaaagtacta      60
attaccaaag tggatccgaa gccgaggaag ggcatggcat ccgtcgcagt ggacttactc     120
gagaaggcct ttgtatacct attgtccgga aattctgcag ctgatcgtag tagtagtagt     180
ggtcgtcgtc gtcgtaaaga gcattactac ctctccggca attatgcgcc cgtcggacac     240 gaaacccgc cctccgacca cctccccatt catggatccc ttcctgaatg cttgaatgga     300
gtgtttctga gagttggtcc taaccccaag tttgctcccg tagccggata caattgggtc     360
gatggagatg gaatgattca tggattgcgt attaaagatg gaaaagcaac ttatctatct     420
cgatatatta aaacgtcacg gtttaaacaa gaagaatatt ttggaagagc aaaatttatg     480
aagattggag atctaagggg attgcttggg ttctttacga tcttaatact agtacttcga     540
acaacattga aagtaataga catttcatat ggaagaggga cgggtaatac agctcttgtg     600
tatcataatg gcttactatt ggctctatca gaagaagata aaccttatgt tgttaaagtt     660
```

-continued

```
ttagaagatg gagacttgca aactcttggg atattggatt atgacaagaa attgtcacat    720
ccattcaccg ctcatccaaa gatcgatccg ttaactgatg agatgtttac ctttggatat    780
tccatctcgc ctccgtatct tacttatcga gtcatttcca aggatggagt gatgcaagat    840
ccagtgcaaa tctcaattac atcccctacc ataatgcatg attttgctat tactgaaaat    900
tatgccatct tcatggacct gcccttgtat ttccaaccag aggaaatggt aaagggaaa     960
tttgtctctt catttcaccc tacaaaaaga gctcgtatcg gtgtgcttcc acgatatgca    1020
aaagacgagc atccaattcg atggttcgat cttccaagtt gcttcatgac tcataatgca    1080
aatgcttggg aagagaatga tgaagttgtg ctattcacat gtcgccttga gagtcctgat    1140
cttgacatgc ttagtggacc tgcggaagaa gagattggga attcaaaaag tgagctttac    1200
gaaatgaggt tcaatttgaa aactggaatt acttcacaaa agcaactatc tgtacctagt    1260
gttgattttc ctcggatcaa ccaaagttat actggcagga acagcaata tgtttattgt     1320
actcttggca acaccaagat taagggcatt gtgaagtttg atctgcaaat tgaaccagaa    1380
gccggaaaga caatgcttga agttggagga aatgtacaag catctttga gttgggacct     1440
agaagatatg gttcagaggc aatatttgtg ccatgccaac ctggcatcaa atctgatgag    1500
gatgacggtt acttgatatt cttttgtacac gacgaaaaca atgggaaatc tgaggtcaat    1560
gtcatcgatg caaagacaat gtctgcagaa cctgtggctg ttgtggaact tccaagcagg    1620
gttccatatg gattccatgc cttgtttctg aatgaggaag aacttcagaa gcaccaagca    1680
gagacatga                                                           1689
```

<210> SEQ ID NO 2
<211> LENGTH: 1123
<212> TYPE: PRT
<213> ORGANISM: Crocus sativus

<400> SEQUENCE: 2

```
Met Ala Asn Lys Glu Glu Ala Glu Lys Arg Lys Lys Pro Lys Pro
1               5                   10                  15

Leu Lys Val Leu Ile Thr Lys Val Asp Pro Lys Pro Arg Lys Gly Met
                20                  25                  30

Ala Ser Val Ala Val Asp Leu Leu Glu Lys Ala Phe Val Tyr Leu Leu
            35                  40                  45

Ser Gly Asn Ser Ala Ala Asp Arg Ser Ser Ser Gly Arg Arg Arg
        50                  55                  60

Arg Lys Glu His Tyr Tyr Leu Ser Gly Asn Tyr Ala Pro Val Gly His
65                  70                  75                  80

Glu Thr Pro Pro Ser Asp His Leu Pro Ile His Gly Ser Leu Pro Glu
                85                  90                  95

Cys Leu Asn Gly Val Phe Leu Arg Val Gly Pro Asn Pro Lys Phe Ala
            100                 105                 110

Pro Val Ala Gly Tyr Asn Trp Val Asp Gly Asp Gly Met Ile His Gly
        115                 120                 125

Leu Arg Ile Lys Asp Gly Lys Ala Thr Tyr Leu Ser Arg Tyr Ile Lys
130                 135                 140

Thr Ser Arg Phe Gln Glu Glu Tyr Phe Gly Arg Ala Lys Phe Met Lys
145                 150                 155                 160

Ile Gly Asp Leu Arg Gly Leu Leu Gly Phe Phe Thr Ile Leu Ile Leu
                165                 170                 175

Val Leu Arg Thr Thr Leu Lys Val Ile Asp Ile Ser Tyr Gly Arg Gly
            180                 185                 190
```

```
Thr Gly Asn Thr Ala Leu Val Tyr His Asn Gly Leu Leu Ala Leu
        195                 200                 205

Ser Glu Glu Asp Lys Pro Tyr Val Lys Val Leu Glu Asp Gly Asp
    210                 215                 220

Leu Gln Thr Leu Gly Ile Leu Asp Tyr Asp Lys Lys Leu Ser His Pro
225                 230                 235                 240

Phe Thr Ala His Pro Lys Ile Asp Pro Leu Thr Asp Glu Met Phe Thr
                245                 250                 255

Phe Gly Tyr Ser Ile Ser Pro Pro Tyr Leu Thr Tyr Arg Val Ile Ser
                260                 265                 270

Lys Asp Gly Val Met Gln Asp Val Gln Ile Ser Ile Thr Ser Pro
                275                 280                 285

Thr Ile Met His Asp Phe Ala Ile Thr Glu Asn Tyr Ala Ile Phe Met
    290                 295                 300

Asp Leu Pro Leu Tyr Phe Gln Pro Glu Glu Met Val Lys Gly Lys Phe
305                 310                 315                 320

Val Ser Ser Phe His Pro Thr Lys Arg Ala Arg Ile Gly Val Leu Pro
                325                 330                 335

Arg Tyr Ala Lys Asp Glu His Pro Ile Arg Trp Phe Asp Leu Pro Ser
                340                 345                 350

Cys Phe Met Thr His Asn Ala Asn Ala Trp Glu Glu Asn Asp Glu Val
                355                 360                 365

Val Leu Phe Thr Cys Arg Leu Glu Ser Pro Asp Leu Asp Met Leu Ser
    370                 375                 380

Gly Pro Ala Glu Glu Ile Gly Asn Ser Lys Ser Glu Leu Tyr Glu
385                 390                 395                 400

Met Arg Phe Asn Leu Lys Thr Gly Ile Thr Ser Gln Lys Gln Leu Ser
                405                 410                 415

Val Pro Ser Val Asp Phe Pro Arg Ile Asn Gln Ser Tyr Thr Gly Arg
                420                 425                 430

Lys Gln Gln Tyr Val Tyr Cys Thr Leu Gly Asn Thr Lys Ile Lys Gly
    435                 440                 445

Ile Val Lys Phe Asp Leu Gln Ile Glu Pro Glu Ala Gly Lys Thr Met
    450                 455                 460

Leu Glu Val Gly Gly Asn Val Gln Gly Ile Phe Glu Leu Gly Pro Arg
465                 470                 475                 480

Arg Tyr Gly Ser Glu Ala Ile Phe Val Pro Cys Gln Pro Gly Ile Lys
                485                 490                 495

Ser Asp Glu Asp Asp Gly Tyr Leu Ile Phe Phe Val His Asp Glu Asn
                500                 505                 510

Asn Gly Lys Ser Glu Val Asn Val Ile Asp Ala Lys Thr Met Ser Ala
    515                 520                 525

Glu Pro Val Ala Val Glu Leu Pro Ser Arg Val Pro Tyr Gly Phe
    530                 535                 540

His Ala Leu Phe Leu Asn Glu Glu Leu Gln Lys His Gln Ala Glu
545                 550                 555                 560

Thr Met Ala Asn Lys Glu Glu Ala Glu Lys Arg Lys Lys Pro Lys
                565                 570                 575

Pro Leu Lys Val Leu Ile Thr Lys Val Asp Pro Lys Pro Arg Lys Gly
                580                 585                 590

Met Ala Ser Val Ala Val Asp Leu Leu Glu Lys Ala Phe Val Tyr Leu
    595                 600                 605
```

-continued

```
Leu Ser Gly Asn Ser Ala Ala Asp Arg Ser Ser Ser Gly Arg Arg
    610                 615                 620

Arg Arg Lys Glu His Tyr Tyr Leu Ser Gly Asn Tyr Ala Pro Val Gly
625                 630                 635                 640

His Glu Thr Pro Pro Ser Asp His Leu Pro Ile His Gly Ser Leu Pro
                645                 650                 655

Glu Cys Leu Asn Gly Val Phe Leu Arg Val Gly Pro Asn Pro Lys Phe
            660                 665                 670

Ala Pro Val Ala Gly Tyr Asn Trp Val Asp Gly Asp Met Ile His
        675                 680                 685

Gly Leu Arg Ile Lys Asp Gly Lys Ala Thr Tyr Leu Ser Arg Tyr Ile
    690                 695                 700

Lys Thr Ser Arg Phe Lys Gln Glu Glu Tyr Phe Gly Arg Ala Lys Phe
705                 710                 715                 720

Met Lys Ile Gly Asp Leu Arg Gly Leu Leu Gly Phe Phe Thr Ile Leu
                725                 730                 735

Ile Leu Val Leu Arg Thr Thr Leu Lys Val Ile Asp Ile Ser Tyr Gly
            740                 745                 750

Arg Gly Thr Gly Asn Thr Ala Leu Val Tyr His Asn Gly Leu Leu Leu
        755                 760                 765

Ala Leu Ser Glu Glu Asp Lys Pro Tyr Val Val Lys Val Leu Glu Asp
    770                 775                 780

Gly Asp Leu Gln Thr Leu Gly Ile Leu Asp Tyr Asp Lys Lys Leu Ser
785                 790                 795                 800

His Pro Phe Thr Ala His Pro Lys Ile Asp Pro Leu Thr Asp Glu Met
                805                 810                 815

Phe Thr Phe Gly Tyr Ser Ile Ser Pro Pro Tyr Leu Thr Tyr Arg Val
            820                 825                 830

Ile Ser Lys Asp Gly Val Met Gln Asp Pro Val Gln Ile Ser Ile Thr
        835                 840                 845

Ser Pro Thr Ile Met His Asp Phe Ala Ile Thr Glu Asn Tyr Ala Ile
    850                 855                 860

Phe Met Asp Leu Pro Leu Tyr Phe Gln Pro Glu Glu Met Val Lys Gly
865                 870                 875                 880

Lys Phe Val Ser Ser Phe His Pro Thr Lys Arg Ala Arg Ile Gly Val
                885                 890                 895

Leu Pro Arg Tyr Ala Lys Asp Glu His Pro Ile Arg Trp Phe Asp Leu
            900                 905                 910

Pro Ser Cys Phe Met Thr His Asn Ala Asn Ala Trp Glu Glu Asn Asp
        915                 920                 925

Glu Val Val Leu Phe Thr Cys Arg Leu Glu Ser Pro Asp Leu Asp Met
    930                 935                 940

Leu Ser Gly Pro Ala Glu Glu Ile Gly Asn Ser Lys Ser Glu Leu
945                 950                 955                 960

Tyr Glu Met Arg Phe Asn Leu Lys Thr Gly Ile Thr Ser Gln Lys Gln
                965                 970                 975

Leu Ser Val Pro Ser Val Asp Phe Pro Arg Ile Asn Gln Ser Tyr Thr
            980                 985                 990

Gly Arg Lys Gln Gln Tyr Val Tyr Cys Thr Leu Gly Asn Thr Lys Ile
        995                 1000                1005

Lys Gly Ile Val Lys Phe Asp Leu Gln Ile Glu Pro Glu Ala Gly
    1010                1015                1020

Lys Thr Met Leu Glu Val Gly Gly Asn Val Gln Gly Ile Phe Glu
```

|   |   |   | 1025 |   |   |   |   | 1030 |   |   |   |   | 1035 |   |   |
|---|---|---|---|---|---|---|---|---|---|---|---|---|---|---|---|
| Leu | Gly | Pro | Arg | Arg | Tyr | Gly | Ser | Glu | Ala | Ile | Phe | Val | Pro | Cys |
|   |   | 1040 |   |   |   | 1045 |   |   |   |   | 1050 |   |   |   |
| Gln | Pro | Gly | Ile | Lys | Ser | Asp | Glu | Asp | Asp | Gly | Tyr | Leu | Ile | Phe |
|   |   | 1055 |   |   |   | 1060 |   |   |   |   | 1065 |   |   |   |
| Phe | Val | His | Asp | Glu | Asn | Asn | Gly | Lys | Ser | Glu | Val | Asn | Val | Ile |
|   |   | 1070 |   |   |   | 1075 |   |   |   |   | 1080 |   |   |   |
| Asp | Ala | Lys | Thr | Met | Ser | Ala | Glu | Pro | Val | Ala | Val | Val | Glu | Leu |
|   |   | 1085 |   |   |   | 1090 |   |   |   |   | 1095 |   |   |   |
| Pro | Ser | Arg | Val | Pro | Tyr | Gly | Phe | His | Ala | Leu | Phe | Leu | Asn | Glu |
|   |   | 1100 |   |   |   | 1105 |   |   |   |   | 1110 |   |   |   |
| Glu | Glu | Leu | Gln | Lys | His | Gln | Ala | Glu | Thr |   |   |   |   |   |
|   |   | 1115 |   |   |   | 1120 |   |   |   |   |   |   |   |   |